(12) United States Patent
Woods

(10) Patent No.: US 7,127,039 B2
(45) Date of Patent: Oct. 24, 2006

(54) IMAGING PLATE

(75) Inventor: Douglas Woods, Franklin, WI (US)

(73) Assignee: PaloDex Group Oy, Tuusula (FI)

(*) Notice: Subject to any disclaimer, the term of this patent is extended or adjusted under 35 U.S.C. 154(b) by 0 days.

(21) Appl. No.: 10/985,345

(22) Filed: Nov. 10, 2004

(65) Prior Publication Data

US 2006/0098785 A1   May 11, 2006

(51) Int. Cl.
*H05G 1/28* (2006.01)

(52) U.S. Cl. ...................... 378/162; 378/165

(58) Field of Classification Search ........... 378/162, 378/165, 169–175, 182, 166, 185, 4, 19; 250/484.4, 584, 580, 589
See application file for complete search history.

(56) References Cited

U.S. PATENT DOCUMENTS

| | | | |
|---|---|---|---|
| 2,286,748 A * | 6/1942 | Martin | 378/169 |
| 4,236,078 A | 11/1980 | Kotera et al. | |
| 4,239,968 A | 12/1980 | Kotera et al. | |
| 4,698,836 A * | 10/1987 | Minasian | 378/162 |
| 4,764,948 A * | 8/1988 | Hurwitz | 378/165 |
| 4,883,960 A * | 11/1989 | Futamata | 250/589 |
| 5,077,778 A * | 12/1991 | Fabian | 378/162 |
| 5,195,122 A * | 3/1993 | Fabian | 378/165 |
| 5,307,397 A * | 4/1994 | Fabian | 378/162 |
| 5,323,443 A * | 6/1994 | Lary | 378/165 |
| 5,381,017 A * | 1/1995 | Ohta | 250/484.4 |
| 5,394,456 A * | 2/1995 | Livingston | 378/162 |
| 5,576,552 A * | 11/1996 | Rantanen | 250/484.4 |
| 6,198,807 B1 * | 3/2001 | DeSena | 378/165 |
| 6,528,813 B1 | 3/2003 | Yasuda | |
| 2004/0081284 A1 * | 4/2004 | Livingston | 378/162 |

* cited by examiner

*Primary Examiner*—Edward J. Glick
*Assistant Examiner*—Irakli Kiknadze
(74) *Attorney, Agent, or Firm*—Andrus, Sceales, Starke & Sawall, LLP

(57) ABSTRACT

An imaging plate for use in computerized radiography has an individual plate identification adapted to be visible in an X-ray image and a further indication marked visibly on the plate. Imaging plates found to be damaged when the X-ray image is examined can be identified by the visible marking.

3 Claims, 1 Drawing Sheet

IMAGING PLATE

The invention relates to an imaging plate for use in computed radiography.

An imaging plate (IP) used in computed radiography comprises a plate having its active side provided with crystals activated (excited) in response to X-radiation. Excitation brings about development of a latent image on the imaging plate. The state of excitation is discharged by means of a laser beam, the imaging plate releasing energy as photons. The photons are passed by way of a photomultiplier to an AD converter, in which light is converted to digital electric signals to be reconstructed on a computer screen for an image. After reading, the image data left on an imaging plate is deleted by means of powerful light for reusing the deleted imaging plate without noise caused by prior radiography operations. A computed radiography system comprises imaging plates, a reading apparatus for the imaging plates, and a workstation with its display unit. U.S. Pat. No. 6,528,813 discloses an imaging-plate employing system, wherein the imaging plate is held in a cassette case during radiography and its passage to the reading apparatus. An imaging plate has been described in publications U.S. Pat. No. 4,236,078 and U.S. Pat. No. 4,239,968, among others.

An imaging plate used in intraoral radiography is normally kept in a light and moisture resistant protective sleeve and placed in the mouth of a radiographed person for the duration of radiography. This is followed by removing the imaging plate from the protective sleeve and passing it to an image reading apparatus, which produces a digital image displayable e.g. on a computer screen. While in the mouth, the imaging plate runs a risk of becoming scratched or damaged on its active side, caused for example by a dental crown as a result of e.g. accidental biting. Scratches can be difficult to detect visually, yet are visible in a digital image and may interfere with diagnosis. A considerable number of imaging plates can be in service in one place, the search for a defective plate being highly tedious as scratches are not readily visible.

It is an object of the present invention to provide a solution that enables localizing a defective imaging plate in a relatively simple manner.

An imaging plate of the invention is characterized in that the plate comprises an individual imaging plate identification adapted to be visible in an X-ray image to be taken of a radiographed object upon the examination thereof on the screen of a display device, and further that the imaging plate identification is marked visibly on the imaging plate.

Figure 1:
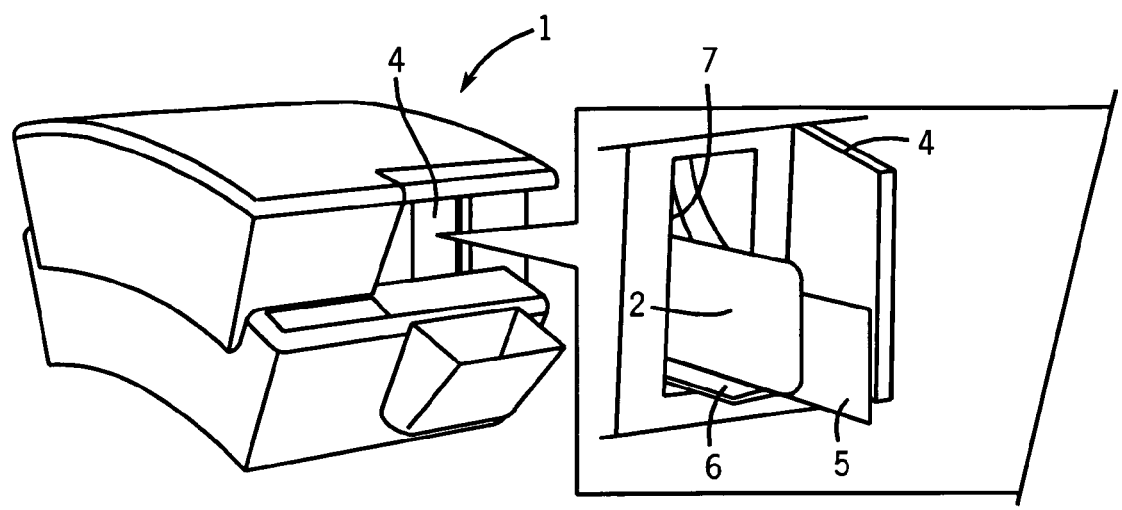
Figure 2:
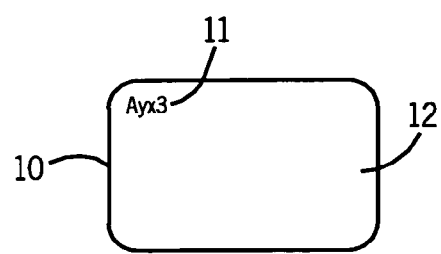
Figure 3:
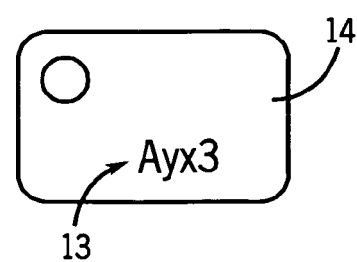

The invention will now be described in more detail with reference to the accompanying drawings, in which:

FIG. 1 shows in a schematic perspective view one prior known imaging plate reading apparatus, FIG. 2 shows one exemplary embodiment for an imaging plate of the invention in a view from the front, and FIG. 3 is the imaging plate of FIG. 1 in a view from behind.

Illustrated in FIG. 1 is an exemplary prior art reading apparatus 1, which houses an imaging plate reading unit and an erasing unit for clearing the imaging plate of residual radiation after reading the image. The reading apparatus 1 is provided with a gate 4, behind which is an imaging plate input slot 7. An imaging plate 2 to be passed into the reading apparatus 1 is placed against brackets 5, 6 emerging out of the slot 7 as the door 4 is opened. The brackets 5, 6 are then passed along with the imaging plate into the reading apparatus and the door 4 closes. The brackets 5, 6 are preferably provided with magnet elements fastening to the edge of an imaging plate.

All reading apparatuses use the same basic technology, but move the plate around a little differently to scan. One system mounts the plates on a spinning drum and a laser is scanned across the drum. Another system uses rollers to move plates past a scanner laser port.

FIG. 2 depicts one imaging plate 10 of the invention, which is provided with an imaging plate identification 11 on an active side 12 of the imaging plate. The identification is designed to be visible in each X-ray image radiographed by using the imaging plate in image examination conducted on a display screen. The IP identification is preferably made "concealed", i.e. in a sufficiently small size not to interfere with diagnosis but capable of being visualised by enlarging an image presently under examination. The IP identification can be e.g. an alphanumerical character, a device character, or e.g. a bar code. FIG. 3 illustrates an imaging plate identification character 13 in a larger size on a reverse side 14 of the imaging plate, whereby it is readily detectable visually in the process of searching a possibly defective imaging plate from among a plurality of imaging plates.

The invention claimed is:

1. An imaging plate device for use in computerized radiography, said device being subject to damage during imaging of a patient, said device comprising:

an imaging plate (10) having an active side (12) receiving x-radiation passing through a radiographed portion of the patient for forming a latent image of a radiographed portion and an x-ray image on a display screen upon examination of the imaging plate in a reading apparatus;

an individual imaging plate identification means (11) on said imaging plate, said individual imaging plate identification means forming an individual imaging plate identification that is visible in the x-ray image obtained from the imaging plate for identifying an individual imaging plate device among other imaging plate devices, said individual imaging plate identification means being of a size and at a location on the imaging plate that does not interfere with the viewing of the x-ray image of the radiographed portion of the patient at normal image enlargement, for diagnostic purposes, but is read at greater than normal enlargement of the location of the individual imaging plate identification means on the imaging plate; and a visible marking (13) of the individual imaging plate identification means on said imaging plate, whereby an imaging plate device found to be damaged from an examination of the x-ray image obtained from the imaging plate is identified from the individual imaging plate identification present in the x-ray image and the identity of the damaged imaging plate device thereafter is determined from the visible marking of the individual imaging plate identification on the imaging plate.

2. An imaging plate device as set forth in claim 1 wherein said individual imaging plate identification means is on one side of said imaging plate and said visible marking is on the other side of said imaging plate.

3. An imaging plate device as set forth in claim 2 wherein said individual imaging plate identification means is on said active side of said imaging plate and said visible marking is on the reverse side (14) of said imaging plate.

* * * * *